US012758692B2

(12) United States Patent
Mooneyham et al.

(10) Patent No.: US 12,758,692 B2
(45) Date of Patent: Oct. 13, 2026

(54) HEATED BREAST SHIELD

(71) Applicant: Momease Solutions, Inc., Plymouth, MN (US)

(72) Inventors: Ashley Mooneyham, Plymouth, MN (US); Jennie Lynch, St. Paul, MN (US); Loic Van Horne, Minneapolis, MN (US)

(73) Assignee: Momease Solutions, Inc., Plymouth, MN (US)

( * ) Notice: Subject to any disclaimer, the term of this patent is extended or adjusted under 35 U.S.C. 154(b) by 0 days.

(21) Appl. No.: 19/335,736

(22) Filed: Sep. 22, 2025

(65) Prior Publication Data

US 2026/0144921 A1 May 28, 2026

Related U.S. Application Data

(60) Provisional application No. 63/725,867, filed on Nov. 27, 2024.

(51) Int. Cl.
*A61M 1/06* (2006.01)

(52) U.S. Cl.
CPC ............ *A61M 1/069* (2021.05); *A61M 1/064* (2014.02)

(58) Field of Classification Search
CPC ........ A61M 1/06; A61M 1/062; A61M 1/064; A61M 1/066; A61M 1/069; A61M 1/0697; A61M 2205/3653; A16J 13/00
See application file for complete search history.

(56) References Cited

U.S. PATENT DOCUMENTS 4,673,388 A 6/1987 Schlensog et al.
5,009,638 A 4/1991 Riedweg et al.
6,257,847 B1 * 7/2001 Silver .................. F04B 45/047 604/74
8,075,516 B2 12/2011 Pfenniger et al.
(Continued)

FOREIGN PATENT DOCUMENTS

CN 108310492 A * 7/2018 ............ A61M 1/064
CN 216798371 U1 6/2022
WO 2022214423 A1 10/2022

OTHER PUBLICATIONS

CN_108310492_A_I, machine translation of CN-108310492 (Year: 2018).*

*Primary Examiner* — Wesley G Harris
*Assistant Examiner* — Charles W Nichols
(74) *Attorney, Agent, or Firm* — Headland Law & Strategy; Matthew J. Smyth

(57) ABSTRACT

A kit may include a shield that is configured to be coupled to a breast pump and to seal against a breast of a lactating user and that includes a heating element and a shield energy source; a housing having a housing energy source and comprising a cavity that is configured to receive the shield; and control circuitry. The control circuitry may: (i) cause, during a recharging phase, energy to be transferred from the housing energy source to the shield energy source to recharge the shield energy source; (ii) cause, during a charging phase, energy to be received from an external source and to replenish the housing energy source; (iii) activate, during a pumping phase, the heating element to convert energy stored in the shield energy source to thermal energy that is transferred to the breast of the lactating user; and (iv) regulate the thermal energy.

15 Claims, 5 Drawing Sheets

(56) References Cited

U.S. PATENT DOCUMENTS

| | | | | |
|---|---|---|---|---|
| 9,498,565 | B2 | 11/2016 | Nowroozi et al. | |
| 10,105,474 | B2 | 10/2018 | Barral et al. | |
| 10,758,653 | B2 | 9/2020 | Kumar et al. | |
| 10,857,271 | B2 | 12/2020 | Bartlett et al. | |
| 10,881,155 | B2 | 1/2021 | Hoth | |
| 11,185,619 | B2 | 11/2021 | Chang et al. | |
| 11,246,967 | B2 | 2/2022 | Weber et al. | |
| 11,331,419 | B2 | 5/2022 | Bauer et al. | |
| 11,400,189 | B2 | 8/2022 | Chang et al. | |
| 11,413,379 | B2 | 8/2022 | Barral et al. | |
| 2003/0194603 | A1 * | 10/2003 | Kim | H01M 10/46 429/209 |
| 2008/0312586 | A1 * | 12/2008 | Thommen | A61M 1/064 604/74 |
| 2010/0324477 | A1 * | 12/2010 | Paterson | A61M 1/82 604/74 |
| 2015/0351956 | A1 | 12/2015 | Enderby | |
| 2016/0296682 | A1 | 10/2016 | Phillips et al. | |
| 2019/0240386 | A1 * | 8/2019 | Larsson | A61M 1/066 |
| 2020/0093971 | A1 | 3/2020 | Pargov et al. | |
| 2021/0154382 | A1 | 5/2021 | Bartlett et al. | |
| 2022/0047785 | A1 | 2/2022 | Masucci | |
| 2022/0233753 | A1 | 7/2022 | Bauer et al. | |
| 2023/0025217 | A1 | 1/2023 | Ford | |
| 2023/0405193 | A1 * | 12/2023 | Haft | A61M 1/067 |
| 2024/0091421 | A1 * | 3/2024 | Jiang | A61M 1/0697 |
| 2026/0000908 | A1 * | 1/2026 | Gao | A61N 5/0616 |

* cited by examiner

HEATED BREAST SHIELD

CROSS REFERENCE TO RELATED APPLICATIONS

This application claims priority to U.S. Application Ser. No. 63/725,867, titled "Heated Shield," filed on Nov. 27, 2024. This application incorporates the entire contents of the foregoing application herein by reference.

TECHNICAL FIELD

Various implementations relate generally to heated shields (e.g., breast shields or nipple cushions) for use in pumping or lactation operations.

BACKGROUND

Traditional electric breast pumps that only use suction power to remove milk from a breast may only remove milk closest to the nipple of a breast—which may lead to incomplete extraction and low milk yield, sometimes despite long, uncomfortable pumping sessions. In contrast to such electric breast pumps, a nursing infant uses a combination of suction, warmth (e.g., from its mouth and hands), and movement (e.g., from its jaw and hands against the breast) to efficiently remove milk from the breast.

SUMMARY

In some implementations, a heated breast shield or nipple cushion may be employed by lactating mothers to facilitate or increase the efficiency of breast pumping. In particular, such a shield may be configured to apply heat to the breast of a lactating mother in a manner that may stimulate milk release during pumping or feeding.

A kit may include a shield that is configured to be coupled to a breast pump and to seal against a breast of a lactating user, the shield comprising a heating element and a shield energy source; a housing having a housing energy source and comprising a cavity that is configured to receive the shield; and control circuitry. The control circuitry may cause, during a recharging phase, energy to be transferred from the housing energy source to the shield energy source to recharge the shield energy source. During a charging phase, the control circuitry may cause energy to be received from an external source and to replenish the housing energy source. During a pumping phase in which the shield is removed from housing and applied to the breast of the lactating user, the control circuitry may activate the heating element to convert energy stored in the shield energy source to thermal energy that is transferred to the breast of the lactating user. The control circuitry may regulate the thermal energy that is converted from the energy stored in the shield energy source or delivered to the breast.

The control circuitry may include user-actuatable controls for turning the heating element on or off and for controlling its temperature. The control circuitry may be disposed in the shield. The control circuitry may be disposed in the housing. The kit may further include a wireless interface that couples the housing to the shield, such that control inputs received at the housing are relayed to the shield to control an on/off state or a temperature of the shield.

The shield energy source may be a chemical battery with an exothermic chemical-to-electrical conversion process. The chemical battery may be an alkaline battery, a zinc air battery, an alkaline zinc-manganese dioxide battery or a lithium metal battery. The chemical battery may be a lithium-ion battery or a nickel-metal-hydride battery. The shield energy source may be electrically coupled to the shield with a tethering cable having a length of at least 12 inches, to enable the shield energy source to be disposed away from the shield. The tethering cable may be a Universal Serial Bus cable coupled at an end opposite the shield to a power brick, or a direct current supply cable coupled at an end opposite the shield to a plug-in alternating current adapter.

The kit may include a second shield, and the cavity may accommodate the shield and the second shield in a clamshell configuration. The cavity may accommodate the shield and second shield in a nested manner.

The shield may include a thermal mass that is configured to store thermal energy and to transfer the stored thermal energy to the breast when the breast shield is sealed around the breast.

The shield may be configured to engage a distal portion of the lactating user's breast. Alternatively, the shield may be configured to engage only an areola of the lactating user's breast. The shield may include a plastic or other rigid polymer, with a distal edge comprising a softer, more compliant material. The softer, more compliant material may be a soft silicone or rubber.

DETAILED DESCRIPTION

In some implementations, a heated breast shield or nipple cushion may be employed by lactating mothers to facilitate or increase the efficiency of breast pumping. In particular, such a shield (as used throughout, "shield" may encompass both a traditional breast shield or a nipple cushion) may be configured to apply heat to the breast of a lactating mother in a manner that may stimulate milk release during pumping or feeding.

Figure 1A:
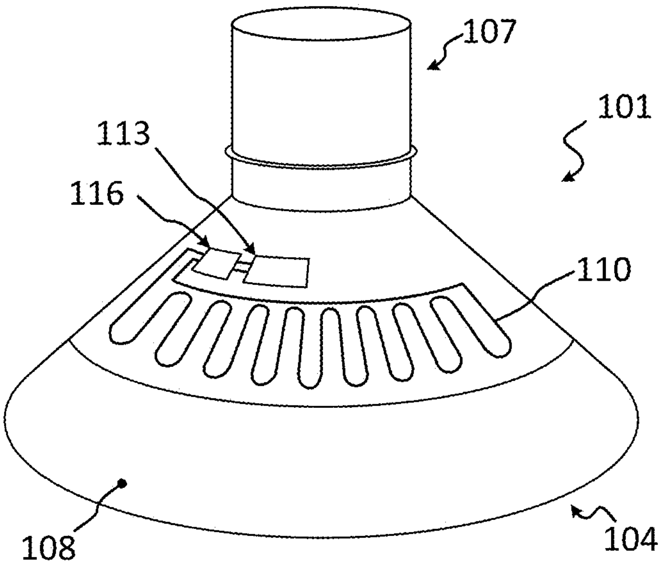
FIG. 1A illustrates an exemplary shield.

FIG. 1A illustrates an exemplary shield 101 that a lactating mother may employ while pumping. In some implementations, as shown, the shield 101 is a breast shield, configured to seal around a breast of the lactating mother. The shield 101 may include a flange end 104 that is open to receive the breast and a port end 107 that is configured to be coupled to a breast pump (e.g., via tubing, not shown). In some implementations, the shield 101 is made of a plastic or other relatively rigid polymer; and a distal edge 108 may be made of a softer, more compliant material, such as a soft silicone or rubber. In other implementations, plastic, silicone, other polymers or combinations of materials may be employed having various levels of elasticity, resilience, softness, smoothness, etc. For example, nipple cushions may include a soft silicone; whereas larger shields may include slightly harder silicone or a combination of soft silicone on the edge and a harder silicone or plastic body.

The shield 101 may include a heating element 110, a shield energy source 113, and shield control circuitry 116. In some implementations, the shield energy source 113 is a rechargeable energy storage device, such as a lithium-ion battery. In other implementations, the shield energy source 113 is a connector for coupling to an external energy source (e.g., a Universal Serial Bus (USB) connector for coupling to a power cube, a 3.5 mm DC plug for receiving external power, a connector configured to receive energy from another device with which it interfaces, such as a powered breast pump and integrated shield, etc.). As shown, the shield energy source 113 is shown attached to the shield 101; but in some implementations, the shield energy source 113 may be electrically connected to the shield 101 but physically removable from the shield 101 (e.g., a battery pack 113 may be electrically tethered to the shield 101 but removable such that it can rest in a user's lap, or include a lapel clip to facilitate clipping to clothing, to, for example, reduce the weight on the shield 101). The shield control circuitry 116 may regulate conversion of electrical energy in the shield energy source 113 to thermal energy in the heating element 110.

In some implementations, the shield energy source 113 may be selected for discharge properties that are particularly efficient in this context. For example, certain chemical batteries (e.g., alkaline, zinc-air, alkaline zinc-manganese dioxide, lithium metal, etc.) have exothermic chemical-to-electrical conversion properties; and this heat may be advantageously employed to provide further warming—in addition to the warming from the electrical energy applied to the heating element 110.

Figure 1B:
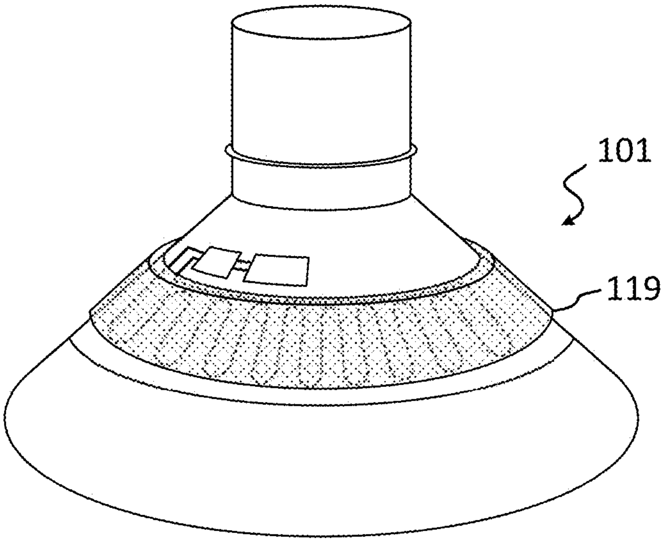
FIG. 1B illustrates an exemplary shield that includes a thermal mass.

In some implementations, as depicted in FIG. 1B, a shield 101 may include a thermal mass 119 that is configured to store and release thermal energy. Such a thermal mass 119 may smooth out delivery of thermal energy from the heating element 110. Moreover, in some implementations, as will be described below, the thermal mass 119 may be preheated (e.g., by the heating element 110 or by another heating element using power from a source other than the shield energy source 113), facilitating delivery of a greater quantity of thermal energy than may be otherwise possible with just the shield energy source 113 and the heating element 110.

In FIG. 1B, the thermal mass 119 is depicted as being disposed external to the body of the shield 101. In other implementations, the thermal mass 119 may be disposed inside the body of the shield 101 (e.g., in contact with the breast). In still other implementations, thermal mass may be provided by the shield materials themselves. In some implementations, any thermal mass 119 may have a reflective skin or an insulative layer that reflects heat toward the breast and limits heat escape away from the breast.

Although a breast shield is depicted in the implementations of FIGS. 1A and 1B, the shield may be smaller in other implementations and may be configured to seal around a smaller portion of a user's breast—for example, just the nipple and areola or portion thereof. Rather than including a port for coupling to a breast pump, such a shield may include or comprise a nipple cushion that is configured for contact with a nursing infant (such as the nipple cushion 102 shown in FIG. 1D, which may be used with another, separate breast shield 103—e.g., as an insert to provide increased comfort and, optionally, heat with commercially available breast shields and breast pumps). Such a nipple cushion may have its own active heating element and energy source, such as those described herein with respect to other implementations; or such a nipple cushion may have a thermal mass that is heated by an external source, such as a housing, prior to its use.

Figure 1C:
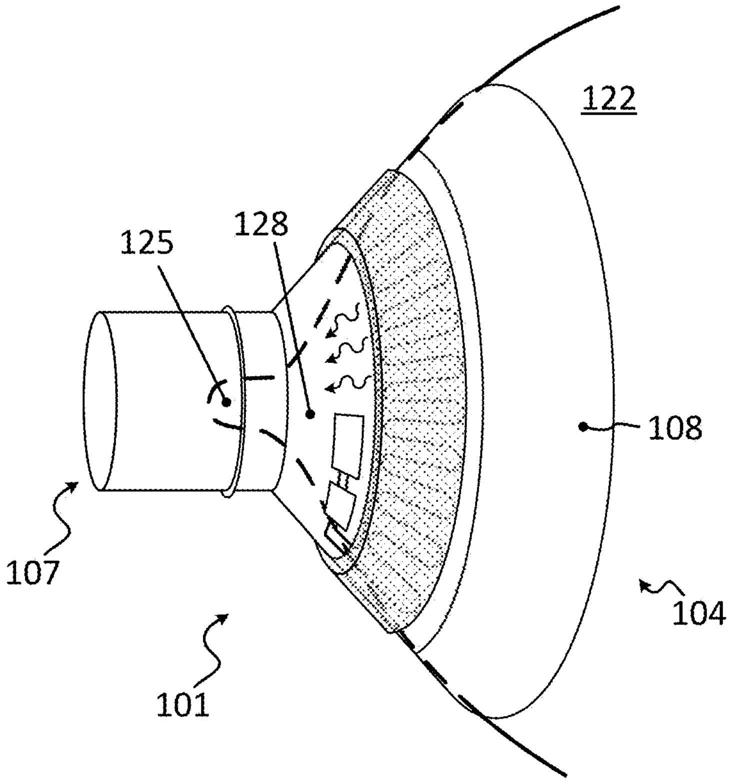
FIG. 1C depicts the exemplary shield of FIG. 1B in use.
Figure 1D:
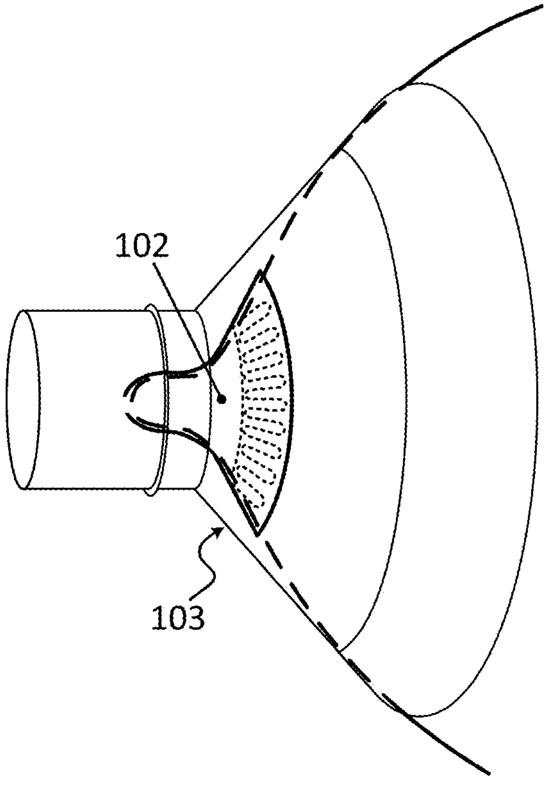
FIG. 1D depicts an exemplary nipple cushion in use with a separate shield.

FIG. 1C illustrates the shield 101 in use. As shown, the flange end 104 of the shield 101 receives the breast 122, and the distal edge 108 may seal around the breast, such that a vacuum drawn by a breast pump (not shown) effectively extracts milk through the port end 107. In some implementations, the nipple 125 may be drawn partially into the port end 107, and the thermal energy provided by the shield 101 may be directed to the areola 128 and/or distal portion of the breast 122.

Figure 2A:
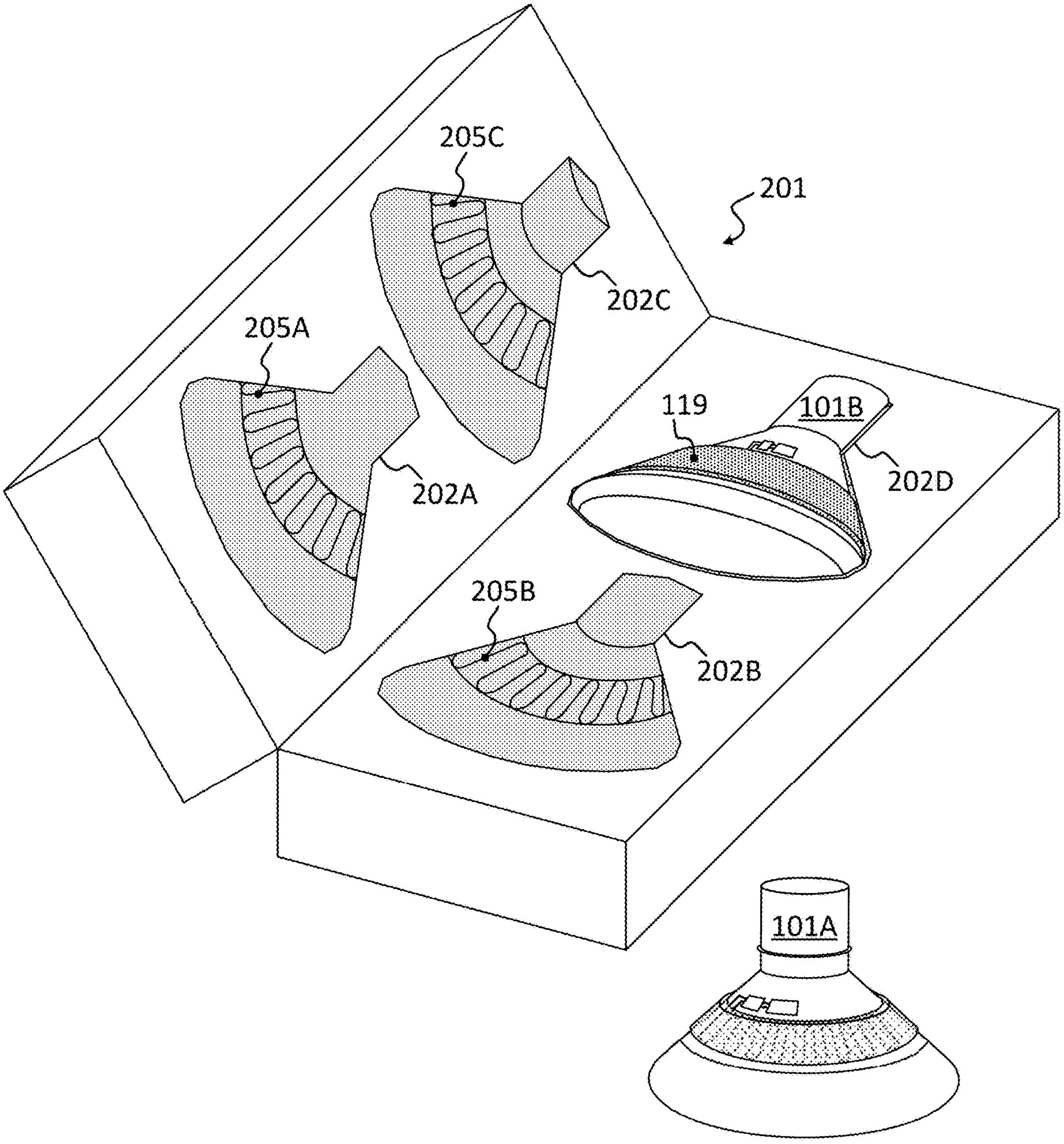
FIG. 2A illustrates an exemplary housing.

FIG. 2A illustrates an exemplary housing 201 that may be used to store one or more shields (e.g., shields 101A and 101B) when not in use. In some implementations, as shown, the housing 201 includes cavities 202A-D that conformably cradle the one or more shields (e.g., in a clamshell manner, as shown, with cavities 202A and 202B configured to cradle a first shield 101A, and with cavities 202C and 202D configured to cradle a second shield 101B).

The housing 201 may further include housing preheating elements (e.g., preheating elements 205A, 205B and 205C; collectively, preheating elements 205). In some implementations, the preheating elements 205 are configured to preheat the shields 101A and 101B when the same are disposed in the housing 201, prior to their use by a lactating mother. The cavities 202A/202B and 202C/202D may be configured to snugly cradle the shields 101A and 101B, so that any thermal mass 119 that is present is in physical contact with the preheating elements 205—such that heat may be efficiently transferred from the preheating elements 205 to the thermal mass 119. In implementations in which there is no discrete thermal mass element 119, or in which thermal mass is provided by the construction and materials of the shields 101A and 101B themselves, portions of the shields 101A and 101B themselves may be in contact with the preheating elements 205 (e.g., portions that are in contact with breast tissue, particularly distal breast tissue). In implementations such as those just described, a preheating operation may be performed using energy from external or housing energy sources (not shown in FIG. 2), rather than the shield energy sources (e.g., energy source 113)—thereby conserving energy in the shield energy source 113 for use when a shield 101 is deployed for pumping, such that additional thermal energy may be delivered during pumping than may be otherwise possible.

Figure 2B:
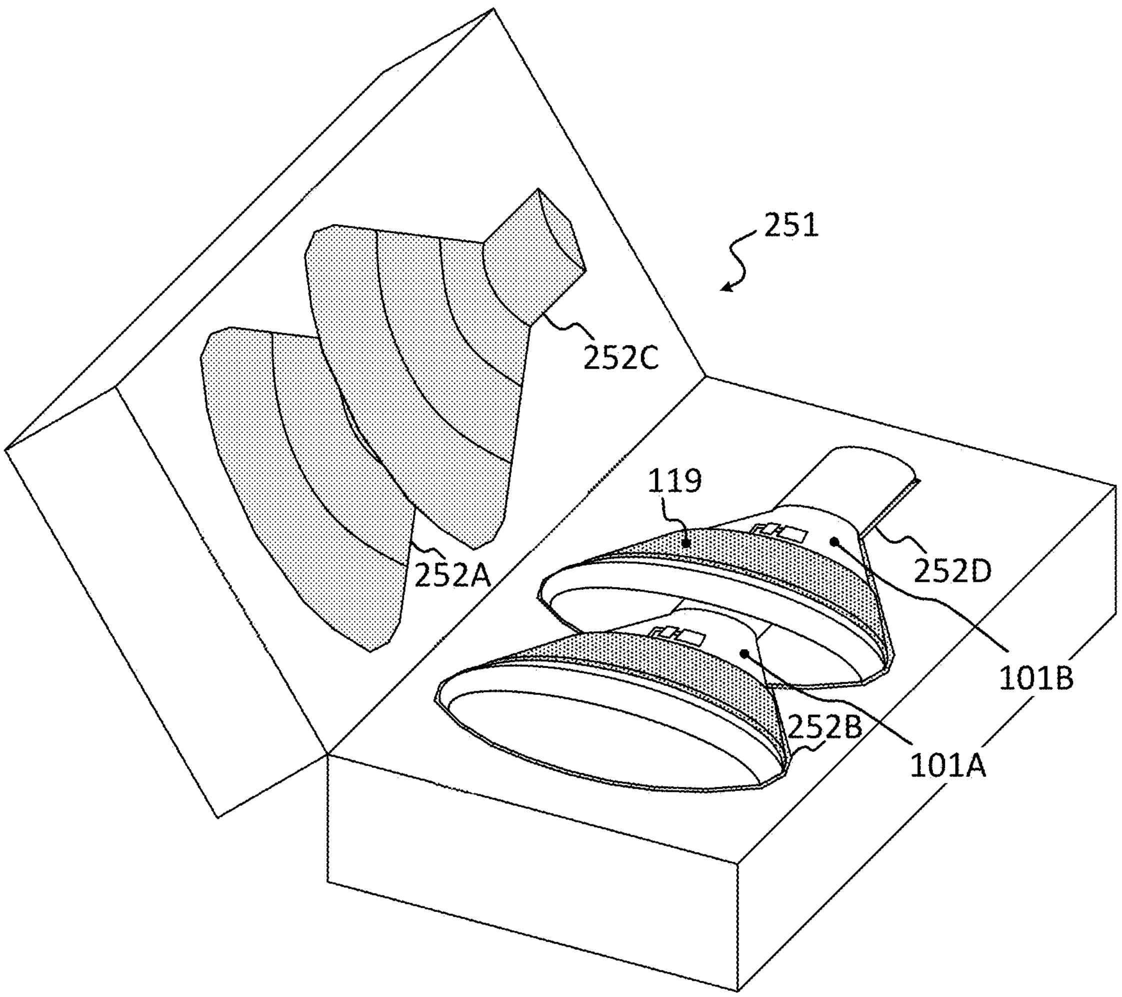
FIG. 2B illustrates another exemplary housing.

FIG. 2B illustrates another exemplary housing 251 that may be used to store one or more shields (e.g., shields 101A and 101B) when not in use. In some implementations, as shown, the housing 251 includes cavities 252A-D that conformably cradle the one or more shields (e.g., in a clamshell manner, as shown, with cavities 252A and 252B configured to cradle the first shield 101A, and with cavities 252C and 252D configured to cradle the second shield 101B). As shown, such an exemplary housing 251 may facilitate nested storage of the shields 101A and 101B, thereby consuming less volume.

The housing 251 may lack the preheating elements shown in the exemplary housing 201 of FIG. 2A. Instead, an implementation such as the one shown in FIG. 2B may be configured to couple a housing energy source or an external energy source directly to the shields 101A and 101B (e.g., inductively, or through electrical contacts (not shown)). In such implementations, preheating of the shields—including any thermal mass 119 that may be included—may still occur within the housing 251, without draining any on-shield energy source.

Figure 3:
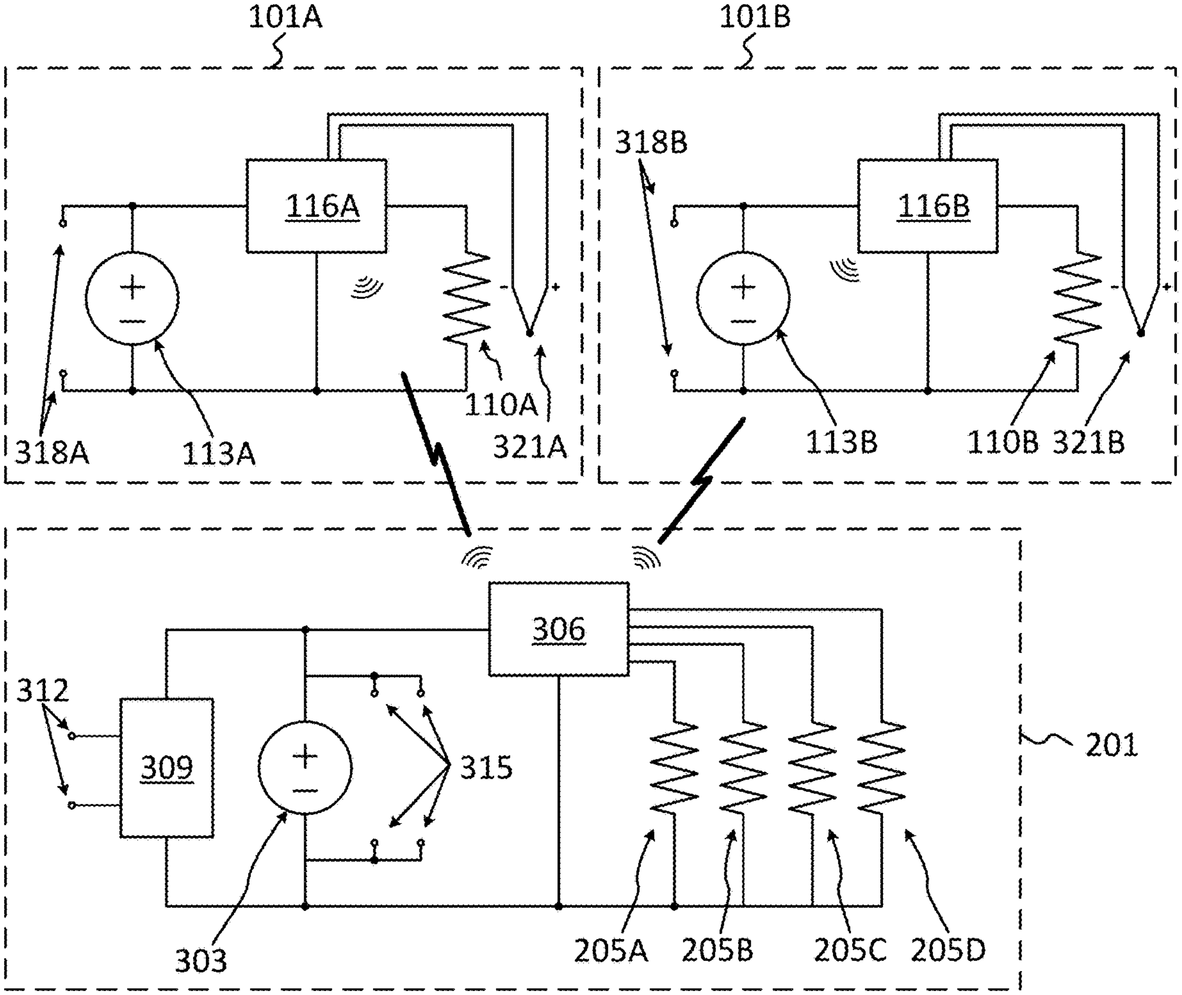
FIG. 3 illustrates exemplary schematics of circuitry in a housing and shields.

FIG. 3 is a schematic illustrating exemplary circuitry in the housing 201 and the shields 101A and 101B. As shown, in one implementation, the housing includes a housing energy source 303, housing control circuitry 306, and housing preheating elements 205A, 205B, 205C and 205D. The housing control circuitry 306 may control delivery of electrical energy from the housing energy source 303 to the preheating elements 205 (e.g., in response to input received from a user interface (not shown)—which may include on/off controls, timers, temperature settings, etc.). As described above, the preheating elements 205 may be activated while shield(s) (e.g., 101A and 101B) are in the housing 201, prior to their use for pumping.

Circuitry in the housing 201 may further include a recharging controller 309 that controls recharging energy received from an external source (e.g., through a charging port 312) and delivered to the housing energy source 303. Further housing ports 315 may be provided for coupling the recharging controller 309 and/or the housing energy source 303 to a shield energy sources 113A and 113B via corresponding shield ports 318A and 318B. Temperature probes 321A and 321B (e.g., thermocouples) may be provided in the shields 101A and 101B, and signals from such probes 321A and 321B may be input to respective controllers 116A and 116B to regulate temperature of the shields 101A and 101B using a closed-loop feedback control circuit. Some implementations may omit the temperature probes 321A and 321B and may use an open-loop control circuit—for example, one in which current is fixed and resistance of heating elements 110 and/or preheating elements 205A, 205B, 205C and 205D is either fixed to facilitate a constant energy transfer, or resistance of the heating elements 110 and/or preheating elements 205A, 205B, 205C and 205D is user-adjustable to modulate temperature. Still other implementations may employ self-regulating circuitry—for example, circuitry in which the resistance of the shield heating elements 110 and/or preheating elements 205A, 205B, 205C and 205D changes with temperature to maintain a constant temperature (e.g., the resistance may increase with increasing temperature and decrease with decreasing temperature).

In some implementations, as depicted, a wireless connection (e.g., a Bluetooth® connection) is provided between the controllers 116A and 116B of the shields 101A and 101B and the controller 306 in the housing 201. In such implementations, a user interface may be included in the housing 201 to enable a user to set temperature of the shields 101A and 101B and to monitor operational parameters (e.g., actual temperature, energy levels in the various energy sources, timers for an automatic shut-off feature, etc.). In some implementations, a system may include other sensors, and information from such sensors may be provided through a user interface (e.g., detected milk volume in the breast, volume of milk expressed, flowrate of milk expressed, etc.).

In some implementations, there may not be a connection between the shields 101A and 101B and the housing 201. In such implementations, or in other implementations, each shield 101A or 101B may have its own user interface (e.g., controls and optional display or indicators that are integrated in control circuitry 116)—enabling a user to activate or deactivate heating functions, control temperature setpoints, monitor actual temperature and energy levels, and view other pumping-related parameters that may be available.

In some implementations, operation may be possible without the housing 201. For example, a shield 101 may include a port for receiving external power, and such external power may perform a preheating function and recharging function directly, without a separate housing 201 with its dedicated circuitry. A shield 101 in such implementations may be unplugged from the external power source when in use, and the shield energy source 113 may provide energy for the shield heating element 110 during pumping.

Several implementations have been described with reference to exemplary aspects, but it will be understood by those skilled in the art that various changes may be made and equivalents may be substituted for elements thereof without departing from the contemplated scope. For example, batteries with various chemistries may be employed, including, for example, lithium iron phosphate batteries, lithium polymer batteries, alkaline batteries, nickel-metal-hydride batteries, lithium-titanium-oxide batteries, lithium/iron disulfide batteries, button cells, etc.; batteries with specific chemistries may be employed that have exothermic discharge reactions—such that heat generated in the process of discharging electrical energy may further contribute to the heating effect within the shields; heating may be direct or indirect—resistive heating elements are depicted, but some implementations may employ indirect heating, for example through infrared or other radiant heating elements; exemplary circuitry has been described, but circuits may be arranged differently—for example, all control circuitry may be present in each shield, and housing circuitry may be omitted, or circuitry may be deployed across shields and housing differently than described; heating element resistance may be fixed, user-adjustable, or temperature-dependent; a kit may include one shield, two shields, or more (e.g., to provide one or more spare shields or to increase the chances that a shield will be fully charged in lengthy or high-demand pumping situations); connections between devices may be wireless, wired, or omitted; various functions may be controllable by users—either on shields themselves, via a housing control panel, or via an app that is linked to the shields or a housing; the housing may be omitted in some implementations; in some implementations, an energy source in the housing may be omitted and only external power may be provided to the housing; in some implementations, the shields may omit a power source and may rely on a thermal mass that is pre-heated in a housing; in some implementations, external power may be provided directly to shields; some implementations may omit the housing; “about,” “approximately” or “substantially” may mean within 1%, or 5%, or 10%, or 20%, or 50%, or 100% of a nominal value; some implementations may be configured as breast shields, while other implementations may be configured as nipple cushions; some such implementations may be configured for stand-alone use, while other implementations (e.g., a nipple cushion implementations) may be configured for use with other, separate systems (e.g., separate breast shields and breast pump systems having various form factors and from various manufacturers).

Many other variations are possible, and modifications may be made to adapt a particular situation or material to the teachings provided herein without departing from the essential scope thereof. Therefore, it is intended that the scope include all aspects falling within the scope of the appended claims.

What is claimed is:

1. A kit comprising:

a shield that is configured to be coupled to a breast pump and to seal against a breast of a lactating user, the shield comprising a resistive heating element, a thermal mass that is configured to store thermal energy and to transfer the stored thermal energy to the breast when the shield is sealed around the breast, and a shield energy source;

a housing having a preheating element and a housing energy source and comprising a cavity that is configured to receive the shield; and a control circuitry;

wherein the control circuitry: (i) causes, during a recharging phase, energy to be transferred from the housing energy source to the shield energy source to recharge the shield energy source; (ii) causes, during a charging phase, energy to be received from an external source and to replenish the housing energy source; (iii) activates, during a preheating phase in which the shield is conformably cradled by the housing, the preheating element to convert energy stored in the housing energy source to thermal energy that is transferred to and stored in the thermal mass; (iv) activates, during a pumping phase in which the shield is removed from the housing and applied to the breast of the lactating user, the resistive heating element to convert energy stored in the shield energy source to thermal energy that is transferred to the breast of the lactating user; and (v) regulates the thermal energy that is converted from the energy stored in the shield energy source or delivered to the breast.

2. The kit of claim 1, wherein the control circuitry comprises user-actuatable controls for turning the resistive heating element on or off and for controlling its temperature.

3. The kit of claim 1, wherein the shield energy source is a chemical battery with an exothermic chemical-to-electrical conversion process.

4. The kit of claim 3, wherein the chemical battery comprises an alkaline battery, a zinc air battery, an alkaline zinc-manganese dioxide battery or a lithium metal battery.

5. The kit of claim 3, wherein the chemical battery comprises an alkaline battery, a zinc air battery, an alkaline zinc-manganese dioxide battery, a lithium metal battery, a lithium-ion battery or a nickel-metal-hydride battery.

6. The kit of claim 1, wherein the control circuitry is disposed in the shield.

7. The kit of claim 1, wherein the control circuitry is disposed in the housing, the kit further comprising a wireless interface that couples the housing to the shield, such that control inputs received at the housing are relayed to the shield to control an on/off state or a temperature of the shield.

8. The kit of claim 1, further comprising a second shield, wherein the cavity accommodates the shield and the second shield in a clamshell configuration.

9. The kit of claim 1, wherein the shield is configured to engage a distal portion of the lactating user's breast.

10. The kit of claim 1, wherein the shield is configured to engage only an areola of the lactating user's breast.

11. The kit of claim 1, wherein the shield comprises a plastic or other rigid polymer, with a distal edge comprising a softer, more compliant material.

12. The kit of claim 11, wherein the softer, more compliant material comprises a soft silicone or rubber.

13. The kit of claim 1, wherein the shield energy source is electrically coupled to the shield with a tethering cable having a length of at least 12 inches, to enable the shield energy source to be disposed away from the shield.

14. The kit of claim 13, wherein the tethering cable comprises at least one of a Universal Serial Bus cable coupled at an end opposite the shield to a power brick, or a direct current supply cable coupled at an end opposite the shield to a plug-in alternating current adapter.

15. A kit comprising:

a breast shield that is configured to be coupled to a breast pump and to seal around a breast of a lactating user, the breast shield comprising a resistive heating element, a breast-shield energy source, and a thermal mass that is configured to store thermal energy and transfer stored thermal energy to the breast when the breast shield is sealed around the breast;

a housing comprising a preheating element, a housing energy source, and a cavity that is configured to conformably cradle the breast shield; and a control circuitry;

wherein the control circuitry: (i) causes, during a recharging phase, energy to be transferred from the housing energy source to the breast-shield energy source to recharge the breast-shield energy source; (ii) causes, during a charging phase, energy to be received from an external source and to replenish the housing energy source; (iii) activates, during a preheating phase in which the breast shield is conformably cradled by the housing, the preheating element to convert energy stored in the housing energy source to thermal energy that is transferred to and stored in the thermal mass; (iv) activates, during a pumping phase in which the breast shield is removed from the housing and applied to the breast of the lactating user, the resistive heating element to convert energy stored in the breast-shield energy source to thermal energy that is transferred to the breast of the lactating user and to the thermal mass; and (v) regulates the thermal energy that is converted from the energy stored in the housing energy source, converted from the energy stored in the breast-shield energy source or delivered to the breast or the thermal mass.

* * * * *